(12) United States Patent
Bäck et al.

(10) Patent No.: US 9,301,551 B2
(45) Date of Patent: Apr. 5, 2016

(54) PANT

(75) Inventors: Lucas Bäck, Billdal (SE); Joshua Carney, Göteborg (SE); Kent Vartiainen, Lerum (SE); Kresten Karlsen, Silkeborg (DK)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/389,289

(22) PCT Filed: Mar. 30, 2012

(86) PCT No.: PCT/SE2012/050354
§ 371 (c)(1),
(2), (4) Date: Dec. 30, 2014

(87) PCT Pub. No.: WO2013/147658
PCT Pub. Date: Oct. 3, 2013

(65) Prior Publication Data
US 2015/0181947 A1 Jul. 2, 2015

(51) Int. Cl.
*A41B 9/12* (2006.01)
*A41B 9/00* (2006.01)
(Continued)

(52) U.S. Cl.
CPC . *A41B 9/12* (2013.01); *A41B 9/004* (2013.01); *A41B 9/04* (2013.01); *A61F 13/15268* (2013.01); *A61F 13/47* (2013.01); *A61F 13/49003* (2013.01); *A61F 13/49006* (2013.01);
(Continued)

(58) Field of Classification Search
CPC ...... A61F 13/49; A61F 13/49009; A41B 9/04

USPC ............................................. 604/385.24, 397
See application file for complete search history.

(56) References Cited

U.S. PATENT DOCUMENTS 2,056,639 A * 10/1936 Wipperman .................. 450/104
2,125,482 A * 8/1938 Barnes ......................... 450/132
(Continued)

FOREIGN PATENT DOCUMENTS

EP          0 073 183 A1    8/1982
JP          2011-025007 A   2/2011
(Continued)

OTHER PUBLICATIONS

JPO Japanese to English Machine translation of Takao et al. JP 2011-25007 (original reference provided by applicant) translated Jun. 15, 2015.*
(Continued)

*Primary Examiner* — Richale Quinn
*Assistant Examiner* — Anne Kozak
(74) *Attorney, Agent, or Firm* — Buchanan Ingersoll & Rooney PC (57) ABSTRACT

A pant—includes front part, a back part and a crotch part, a waist portion and a pair of leg openings. The pant further includes a suspending member formed of elastic material and comprising zones of different elasticity. A first elastic zone having a relatively higher elongation is provided in a longitudinally extending central region of the crotch part, and a pair of second elastic zones having a relatively lower elongation extend along both sides of the first elastic zone at or close to the leg openings in the crotch part. The first and second elastic zones extend to the front part with the second elastic zones extending along both sides of the first zone.

20 Claims, 6 Drawing Sheets

(51) Int. Cl.

| | | |
|---|---|---|
| *A61F 13/47* | (2006.01) | |
| *A61F 13/505* | (2006.01) | |
| *A41B 9/04* | (2006.01) | |
| *A61F 13/49* | (2006.01) | |
| *A61F 13/56* | (2006.01) | |
| *A61F 13/15* | (2006.01) | |
| *A61F 13/514* | (2006.01) | |

(52) U.S. Cl.
CPC ..... *A61F 13/49011* (2013.01); *A61F 13/49015* (2013.01); *A61F 13/49019* (2013.01); *A61F 13/505* (2013.01); *A61F 13/5605* (2013.01); *A61F 2013/51449* (2013.01)

(56) References Cited

U.S. PATENT DOCUMENTS

| | | | | |
|---|---|---|---|---|
| 2,344,374 | A * | 3/1944 | Stephens | 450/104 |
| 2,494,261 | A * | 1/1950 | Owenby | 2/401 |
| 3,687,141 | A * | 8/1972 | Matsuda | 604/396 |
| 3,852,828 | A * | 12/1974 | Silverstein | 2/401 |
| 5,291,617 | A * | 3/1994 | Moretz et al. | 2/400 |
| 5,398,346 | A * | 3/1995 | Feinberg et al. | 2/400 |
| 5,669,902 | A * | 9/1997 | Sivilich | 604/396 |
| 5,855,573 | A * | 1/1999 | Johansson | 604/385.17 |
| 5,888,118 | A * | 3/1999 | Kishi | 450/122 |
| 5,954,564 | A * | 9/1999 | Ganz | 450/99 |
| 6,041,446 | A * | 3/2000 | Braunstein et al. | 2/400 |
| 6,287,169 | B1 * | 9/2001 | Willms et al. | 450/101 |
| 6,626,883 | B2 * | 9/2003 | Wada et al. | 604/396 |
| 6,807,685 | B1 * | 10/2004 | Hasegawa et al. | 2/406 |
| 7,260,961 | B1 | 8/2007 | Kennedy | |
| 7,685,651 | B2 * | 3/2010 | Yoo | 2/403 |
| 7,774,865 | B2 * | 8/2010 | Miller | 2/403 |
| 7,785,309 | B2 * | 8/2010 | Van Gompel et al. | 604/385.101 |
| 7,875,014 | B2 * | 1/2011 | Hendren et al. | 604/396 |
| D672,530 | S * | 12/2012 | Williams | D2/738 |
| D684,748 | S * | 6/2013 | Carney et al. | D2/712 |
| D685,156 | S * | 7/2013 | Carney et al. | D2/712 |
| D702,918 | S * | 4/2014 | Radford et al. | D2/712 |
| 8,752,216 | B2 * | 6/2014 | Sawle et al. | 2/228 |
| D711,070 | S * | 8/2014 | Lecigne | D2/712 |
| D726,393 | S * | 4/2015 | Wexler | D2/712 |
| 2001/0020158 | A1 * | 9/2001 | Nozaki et al. | 604/402 |
| 2001/0025165 | A1 | 9/2001 | Shimoe | |
| 2001/0025386 | A1 * | 10/2001 | Suga et al. | 2/406 |
| 2002/0045872 | A1 | 4/2002 | Shimada et al. | |
| 2004/0006326 | A1 | 1/2004 | Nakajima et al. | |
| 2004/0116881 | A1 * | 6/2004 | Nordness et al. | 604/358 |
| 2005/0131382 | A1 * | 6/2005 | Brud et al. | 604/401 |
| 2005/0148980 | A1 * | 7/2005 | Fitton | 604/385.3 |
| 2005/0197643 | A1 * | 9/2005 | Suga et al. | 604/396 |
| 2005/0256489 | A1 | 11/2005 | Sawyer et al. | |
| 2006/0271009 | A1 * | 11/2006 | Cartier et al. | 604/385.31 |
| 2007/0083985 | A1 * | 4/2007 | Nathan et al. | 2/400 |
| 2008/0119813 | A1 * | 5/2008 | Carstens | 604/385.24 |
| 2008/0184461 | A1 * | 8/2008 | Utaka | 2/406 |
| 2009/0077720 | A1 * | 3/2009 | Shinomiya | 2/401 |
| 2010/0175170 | A1 * | 7/2010 | Dye | 2/406 |
| 2012/0123377 | A1 * | 5/2012 | Back | 604/385.01 |
| 2013/0218118 | A1 * | 8/2013 | Vartiainen | 604/385.24 |
| 2013/0281958 | A1 * | 10/2013 | Back et al. | 604/385.25 |
| 2013/0289512 | A1 * | 10/2013 | Rhodes et al. | 604/385.24 |

FOREIGN PATENT DOCUMENTS

| | | | |
|---|---|---|---|
| WO | WO 2004/075801 A1 | 9/2004 | |
| WO | WO 2009/003486 A1 | 1/2009 | |
| WO | WO 2009003485 A1 * | 1/2009 | A41B 9/12 |

OTHER PUBLICATIONS

"Extend, verb." Merriam-Webster.com. Sep. 2015 Web. Sep. 22, 2015. http://www.merriam-webster.com/dictionary/extend.*
International Search Report (PCT/ISA/210) mailed on Dec. 17, 2012, by the Swedish Patent Office as the International Searching Authority for International Application No. PCT/SE2012/050354.
Written Opinion (PCT/ISA/237) mailed on Dec. 17, 2012, by the Swedish Patent Office as the International Searching Authority for International Application No. PCT/SE2012/050354.
International Preliminary Report on Patentability (PCT/IPEA/409) mailed on Jun. 13, 2014, by the European Patent Office as the International Searching Authority for International Application No. PCT/SE2012/050354.

* cited by examiner

PANT

TECHNICAL FIELD

The present invention refers to a pant adapted to hold an absorbent pad firmly against the body of a wearer.

BACKGROUND OF THE INVENTION

A pant is required to firmly hold an absorbent pad against the body and to prevent the absorbent pad from shifting out of position at the crotch part in order to prevent leakage of body fluid. In a so called two piece system specially designed pants are used, wherein the pant is of washable material, usually textile material, and is adapted to hold a disposable absorbent pad therein, said absorbent pad can be easily attached to and removed from the pant. The pant is usually provided with attachment means adapted to cooperate with corresponding attachment means on the absorbent pad. Said attachment means can be frictional attachment means such as hook-and-loop material. A soiled absorbent pad may thus easily be removed from the pant and replaced with a new pad.

US 2001/0020158 discloses a sanitary pant adapted to hold a sanitary napkin firmly against the body of a wearer. The sanitary pant includes a suspending member formed of stretchable material and extending along the front part, the crotch part and the back part of the pant. The pant further comprises extension cloths extending on both sides of the suspension member. The suspending member has a greater contraction stress than the extension cloth.

US 2005/0197643 discloses a panty adapted to fit a sanitary napkin to the crotch portion, wherein a band-shaped area is provided in the center area of the back part from the crotch part to the waist opening. The band-shaped area is formed of slightly elastic material adapted to press and fit parts of the sanitary napkin to the body of the wearer. Other parts of the pant are made of a highly elastic material.

U.S. Pat. No. 7,260,961 discloses circularly knit undergarments comprising different support panels integrally knitted together.

EP 0 073 183 discloses an elastic pant designed for holding an absorbent pad in place wherein the knitting or crocheting is looser in a central area of the front and back portion and wherein elastic threads are knitted or crocheted along the edges of said central area.

SUMMARY OF THE INVENTION

One object of the present invention is to provide a pant especially a pant forming part of a so called two piece system and thus adapted to hold an absorbent pad, said pant providing support for the absorbent pad and providing security against leakage and also allowing expansion of the absorbent pad when loaded with body fluid. The pant according to the invention comprises a front part, a back part and a crotch part positioned between said front and back parts, a waist portion formed at upper end portions of said front part and said back part and a pair of leg openings. The pant further comprises a suspending member formed of elastic material and extending along at least said crotch part and said front part, wherein said suspending member comprises zones of different elasticity, said pant having a longitudinal (y) and a transverse (x) direction. A first elastic zone having a relatively higher elongation as measured in the longitudinal direction (y) of the pant according to the test method EN 14704-1 as defined herein, is provided in a longitudinally extending central region of the crotch part, and a pair of second elastic zones having a relatively lower elongation as measured in the longitudinal direction (y) of the pant according to the test method EN 14704-1 as defined herein, extend along both sides of said first elastic zone at or close to said leg openings in the crotch part, said first and second elastic zones extending to the front part, with said pair of second elastic zones of a relatively lower elongation extending along both sides of said first zone of a relatively higher elongation also in said front part.

A third elastic zone of a relatively lower elongation as measured in the longitudinal direction (y) of the pant according to the test method EN 14704-1 as defined herein than said first elastic zone may extend longitudinally along a central region of the back part.

Said pair of second elastic zones of relatively lower elongation may diverge from said crotch part to the front part, so that the width (w1) of said first elastic zone of relatively higher elongation is gradually reduced from said front part to said crotch part.

The third elastic zone and the second elastic zones may have the same elongation.

Said pair of second elastic zones of relatively lower elongation may converge to continuously form said third elastic zone.

Said pair of second elastic zones of relatively lower elongation may alternatively be separated from said third elastic zone.

Said third elastic zone of relatively lower elongation in said back part may have a width, w3, that increases towards the upper waist end edges of the back part.

The width, w2, of each of the second elastic zones of a relatively lower elongation in said crotch part may be between 3 and 30 mm.

The second elastic zones of a relatively lower elongation may be located at a distance of between 0 and 20 mm from the respective leg opening in at least part of the crotch part.

The minimum width, w1, in the crotch part of the first elastic zone may be at least 40 mm.

Said first elastic zone may comprise at least two areas of different elasticity, wherein a first area may be located in the crotch part of the pant and a second area may be located in the front part and wherein said first area may have a higher elongation as compared to said second area.

The elongation in the first elastic zone may be between 50% and 400% higher than in the second elastic zones.

The elongation in the first elastic zone may be between 50% and 400% higher than in the third elastic zones.

The first elastic zone may have an elongation at 5N in the range 50% to 300% and the second and/or third elastic zones may have an elongation at 5N in the range 25% to 150%.

Said first elastic zone may have a lower modulus in the load phase and in the return phase as measured in the longitudinal direction (y) of the pant according to the test method EN 14704-1 as defined herein as compared to the second elastic zone.

Said first elastic zone may have a lower modulus in the load phase and in the return phase as measured in the longitudinal direction (y) of the pant according to the test method EN 14704-1 as defined herein, as compared to the third elastic zone.

Said first elastic zone may have a modulus in the load phase between 10 and 50 N/m and a modulus in the return phase between 8 and 40 N/m and said second and/or third elastic zones may have a modulus in the load phase between 40 and 120 N/m and a modulus in the return phase between 25 and 70 N/m.

The modulus in the load phase and in the return phase in the second elastic zones may be between 50% and 600% higher than in the first elastic zone.

Said first, second and third elastic zones may extend to the upper waist end edges of the front and back parts respectively.

The pant may be a reusable washable pant adapted to hold a disposable absorbent pad therein.

The pant may be an inner pant of a boxer shorts which further may comprise an outer garment shell with hanging legs and wherein the inner pant is attached to the outer garment shell at least in a waist portion thereof.

The pant may be provided with fastening means for attachment of an absorbent pad.

The zones of different elasticity may be formed integrally and seamlessly by knitting technique.

DETAILED DESCRIPTION OF PREFERRED EMBODIMENTS

The invention will in the following be closer described with reference to some embodiments shown in the accompanying drawings.

Figure 1:
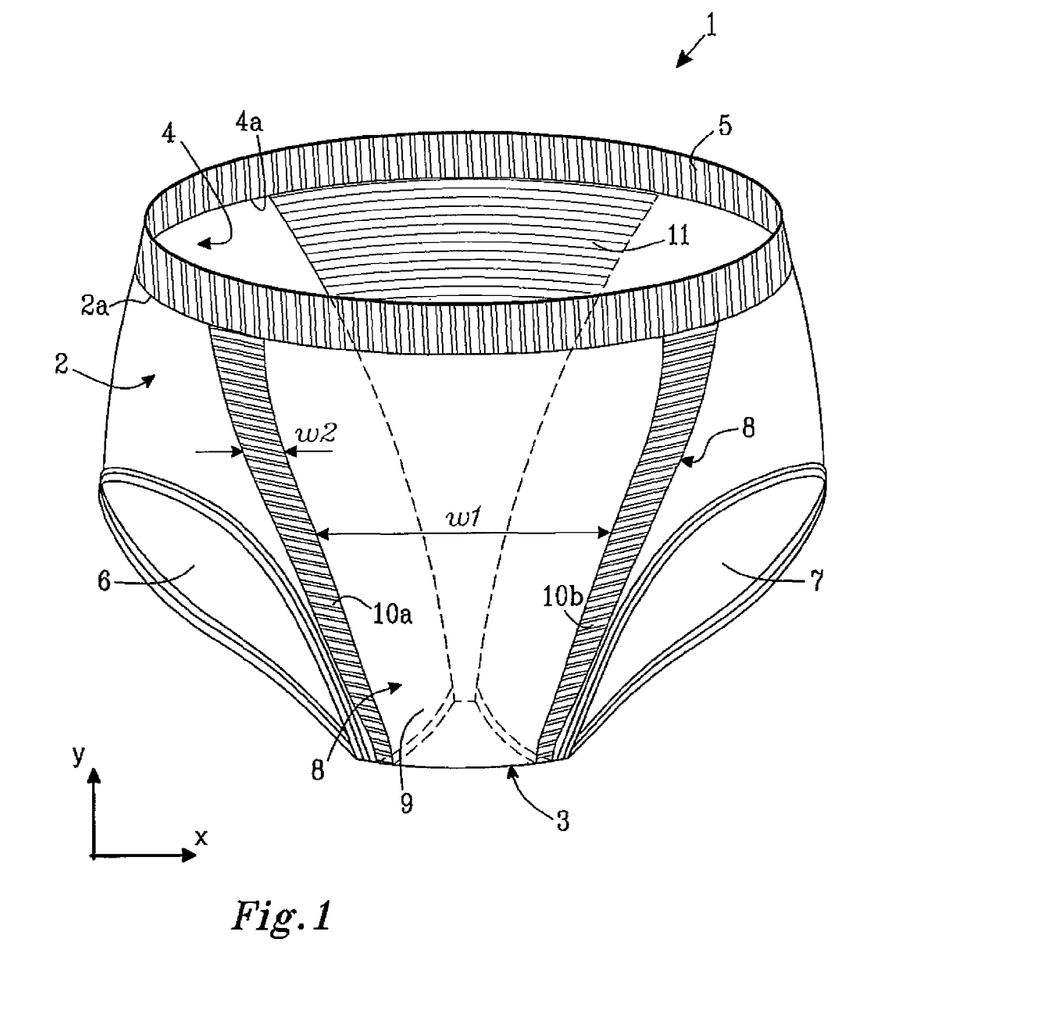
FIG. 1 is a front view of an embodiment of a pant according to the invention.
Figure 2:
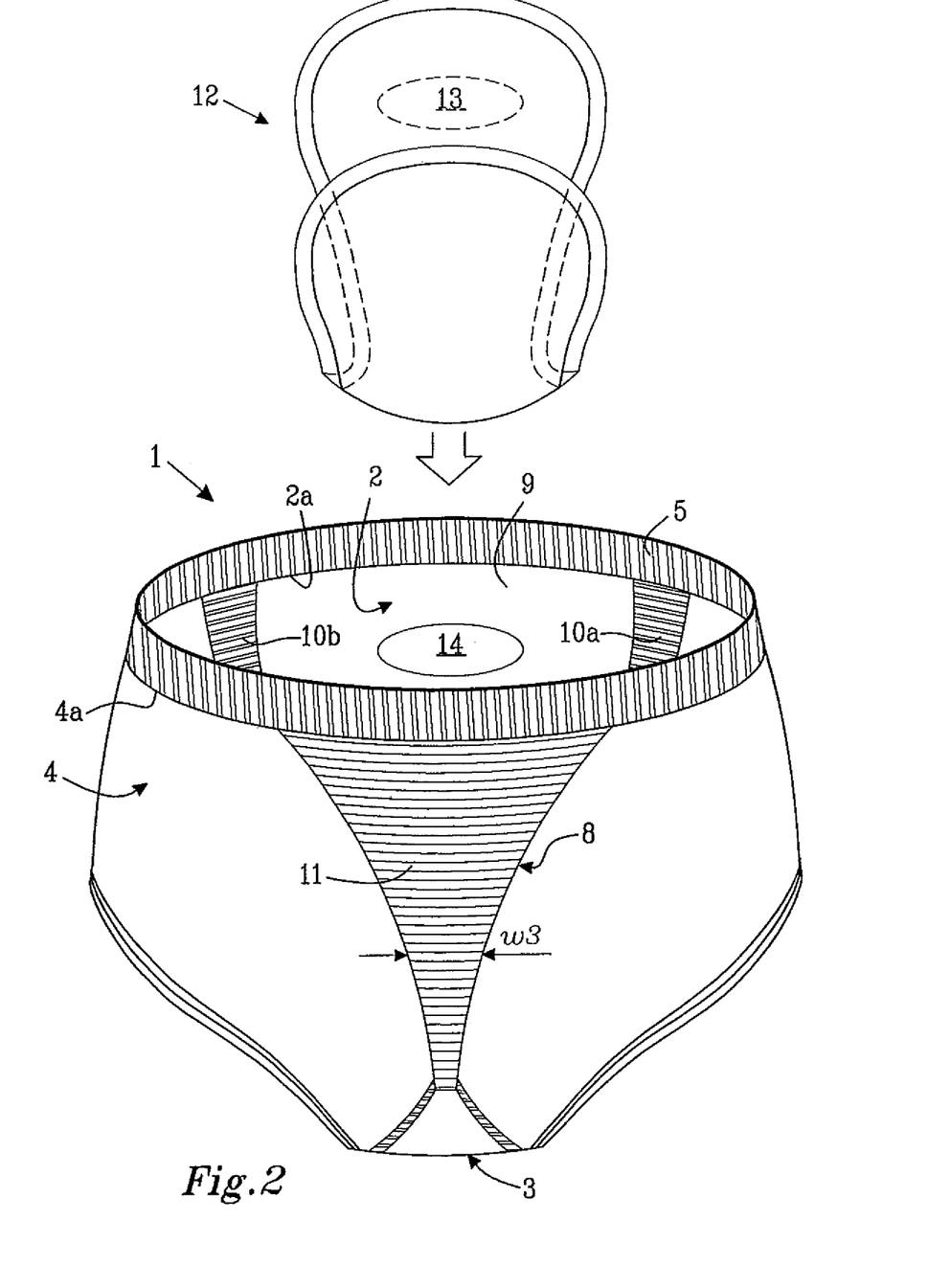
FIG. 2 is a rear view of the pant in FIG. 1 also illustrating an absorbent pad to be inserted into the pant.

FIGS. 1 and 2 shows a first embodiment of a pant 1 according to the invention. The pant resembles an ordinary underwear pant for females. It comprises a front part 2, a crotch part 3 and a back part 4. The longitudinal direction, y, is the direction along which the front part, crotch part and back part extend in series. The transverse direction, x, is the direction transverse to the longitudinal direction, y. A center line extending in the longitudinal direction at a center in the transverse direction is referred to as A-A. A center line extending in the transverse direction at a center in the longitudinal direction is referred to as B-B.

The pant 1 further comprises a waist portion 5 at upper end edges 2a and 4a of said front part 2 and said back part 4. The waist portion 5 may comprise a separate elastic waist band attached to the upper end edges 2a and 4a of the front and rear parts or may alternatively be formed by elastification of the upper end portions of the front and back parts 2 and 4. A pair of leg openings 6 and 7 are formed below joining portions between of said front and said back part. The leg opening areas may optionally be elasticized. Side edges of said front and back parts 2 and 4 may be joined along seams or the front ant back parts may be integrally formed with no seams there between.

The pant further comprises a suspending member 8 formed of elastic material and extending from said front part 2, said crotch part 3 and said back part 4. The suspending member 8 is adapted to hold an absorbent pad in close contact with the body of a wearer. It comprises zones of different elasticity. A first elastic zone 9 having a relatively higher elongation in the longitudinal direction (y) of the pant is provided in a longitudinally extending central region of the crotch part 3 and extends to the front part 2 in a longitudinally extending central region thereof. A pair of second elastic zones 10a and b having a relatively lower elongation in the longitudinal direction (y) of the pant extend along both sides of said first elastic zone 9 at or close to said leg openings 6 and 7 in the crotch part. The elongation is defined as in the test for elasticity according to EN 14704-1 described below.

The first and second elastic zones 10a and b extend to and along the front part 2 along both sides of the first elastic zone 9 of a relatively higher elongation. The pair of second elastic zones 10a and b of relatively lower elongation diverge from the crotch part 3 to the front part 2, so that the width w1 of the first elastic zone 9 of a relatively higher elongation is gradually reduced from the front part 2 to the crotch part 3. The width w1 has a minimum width in the crotch part of at least 40 mm. In the area of the front part 2 located adjacent the waist portion 5 the width w1 may be in the range 60 to 350 mm.

The second elastic zones 10a and b of a relatively lower elongation are located at a distance of between 0 and 20 mm from the respective leg opening 6 and 7 in at least part of the crotch part 3. The width w2 of each of the second zones 10a and b of a relatively lower elongation in said crotch part 3 is between 3 and 30 mm. The width w2 may vary along the crotch part 3 and the front part 2. The width w2 may be greater in the front part and be gradually reduced towards the crotch part.

A third elastic zone 11 of a relatively lower elongation as compared to the first elastic zone 9 extends from the crotch part 3 longitudinally along a central region of the back part 4. The third elastic zone 11 has a width w3 that increases towards the waist portion 5 of the back part 4.

The second elastic zones 10a and b converge towards the third elastic zone 11. The boundary between the second elastic zones and the third elastic zone may vary. In the embodiment shown in FIGS. 1-3 said boundary is located in a back region of the crotch part 3 spaced from the center line B-B in transverse direction. The boundary may be located at said center line B-B or spaced from said center line up to 100 mm towards the back part 4 of the pant. Preferably it is located at a distance between 10 and 70 mm from said center line B-B towards the back part 4.

Figure 3:
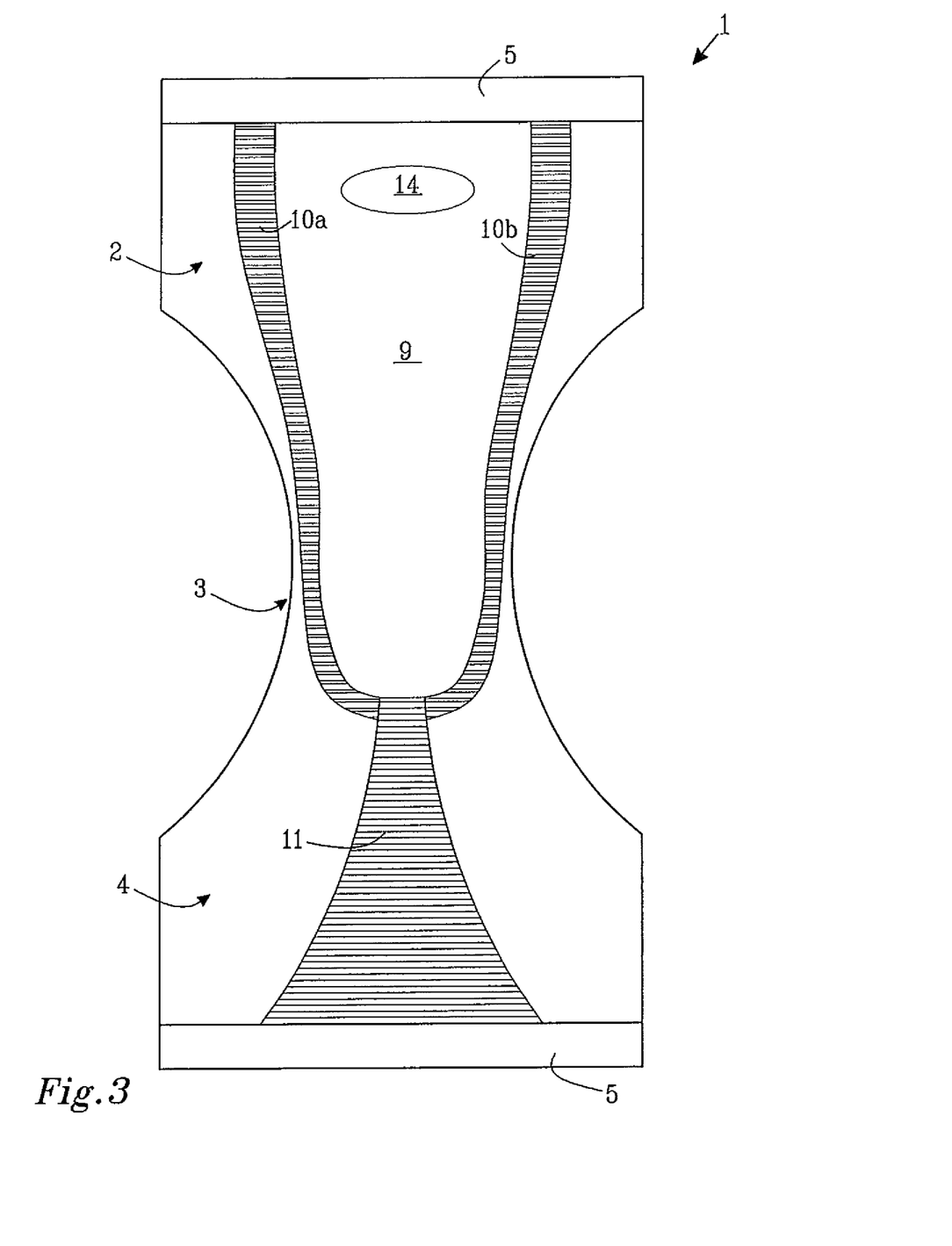
FIG. 3 shows the pant cut open for illustration of features.

The third elastic zone 11 and the second elastic zones 10a and b may have the same elongation and be made in the same way. Alternatively they may have differing elongations.

The areas of the front, crotch and back parts 2, 3 and 4 located outside the suspending member 8 may have the same elongation as the first elastic zone 9 or have a lower elongation than said first elastic zone 9. The different areas of the pant having different elastic properties may be joined together, for example by sewing, or they may be formed integrally and seamlessly by knitting technique known in the art.

Another elastic property measured by the EN 14704-1 test is the modulus in the load phase and in the return phase. The higher modulus, the greater pull and fixation the fabric has. The first elastic zone 9, 9a, 9b should have a relatively lower modulus both in the load and the return phase as compared to the second and third elastic zones 10 and 11.

The difference in elasticity in the different areas can be obtained in a number of different ways, which per se are well-known in the art, such as using different knitting techniques, different type of yarns, different dtex of the yarns and/or different density of the yarn.

The pant is adapted to hold an absorbent pad 12 against the body of a wearer. The absorbent pad 12 may be an incontinence pad or a sanitary napkin. The absorbent pad will not be described in detail and is commonly known in the art. It normally comprises a liquid permeable topsheet material, a liquid impermeable backsheet material and an absorbent member enclosed there between. The absorbent member may comprise so called superabsorbent material with the ability to absorb liquid many times its own weight under swelling.

The absorbent pad 12 may on the garment facing side, i.e. on the backsheet side, have a fastening means 13 intended to match with corresponding fastening means 14 provided on the inside of the pant 1. These fastening means will ensure proper placement of the absorbent pad 12 in the pant and prevent slipping thereof. The fastening means 13 and 14 may be hook-and-loop fasteners or other frictional fasteners. Sometimes the fastening means 14 in the pant can be omitted if the material in the pant provides sufficient friction for the fastening means 13 on the absorbent pad. The fastening means 13 and 14 are in the embodiment illustrated in the drawing located in the front part of the absorbent pad and in the pant.

The absorbent member of the absorbent pad 12 will absorb body fluid under expansion thereof, especially when superabsorbent material is present. The first elastic zone 9 located in a longitudinally extending central region of the crotch part 3 and the front part 2 has a relatively low resistance to stretch, i.e. a relatively high elongation and a relatively low modulus, so that expansion of the absorbent member is not hindered when it absorbs body fluid. The second elastic zones 10a and b in the crotch part 3 and the front part 2 located along both sides of the first elastic zone 9 and having a relatively higher resistance to stretch, i.e. a relatively low elongation and a relatively high modulus, will press the absorbent pad 12 against the body of the wearer and provide a sealing of the absorbent pad towards the body of the wearer to prevent leakage along the edges of the absorbent pad. The third elastic zone 11 located in a longitudinally extending central region of the back part 4 having a higher resistance to stretch, i.e. a relatively lower elongation and a relatively higher modulus, than the first elastic zone 9 presses the absorbent pad against the body to provide a sealing effect also in this area.

The second elastic zones 10a and b and the third elastic zone 12 may extend all the way up to the waist end edges 2a and 4a of the front part 2 and the back part 4 respectively, which are joined to the waist band 5. This will provide a proper tightening of these zones when the pant is pulled up.

Figure 4:
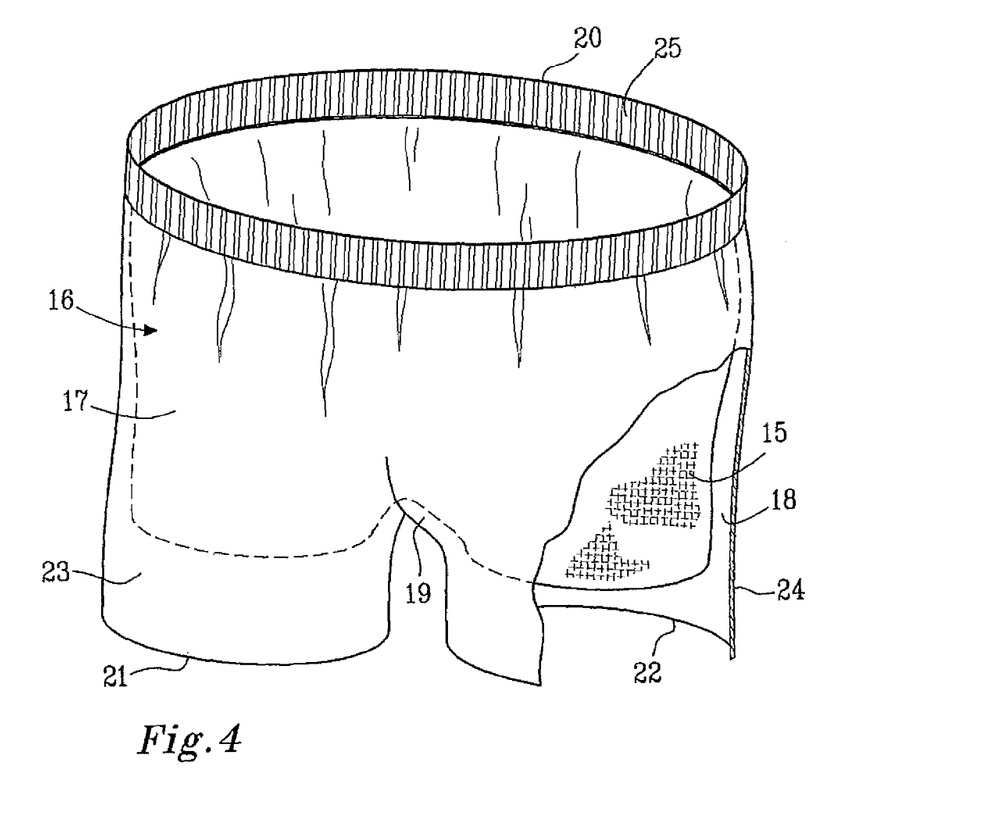
FIG. 4 is a front view of a boxer shorts having an inner pant according to the invention.
Figure 5:
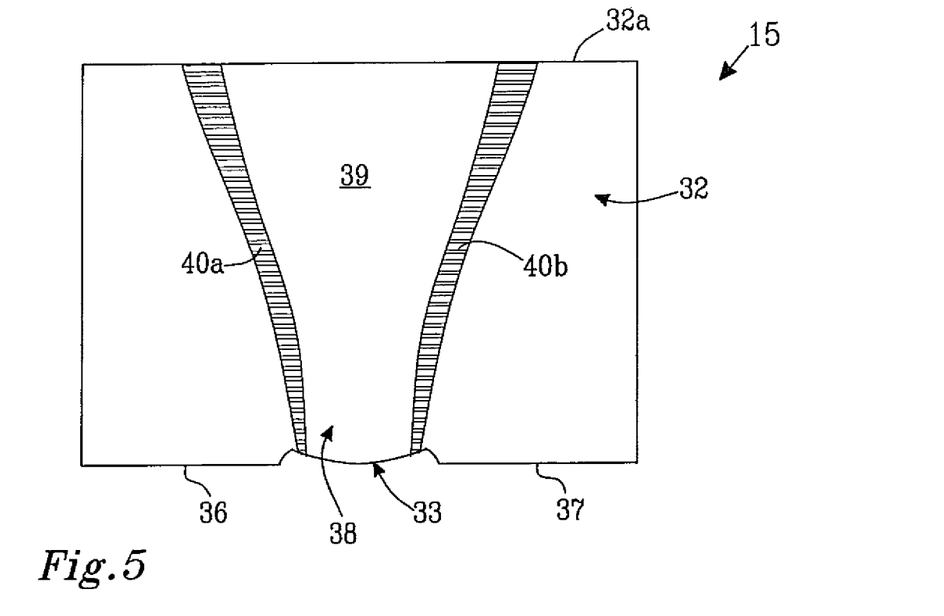
FIG. 5 is a front view of the inner pant in FIG. 4.
Figure 6:
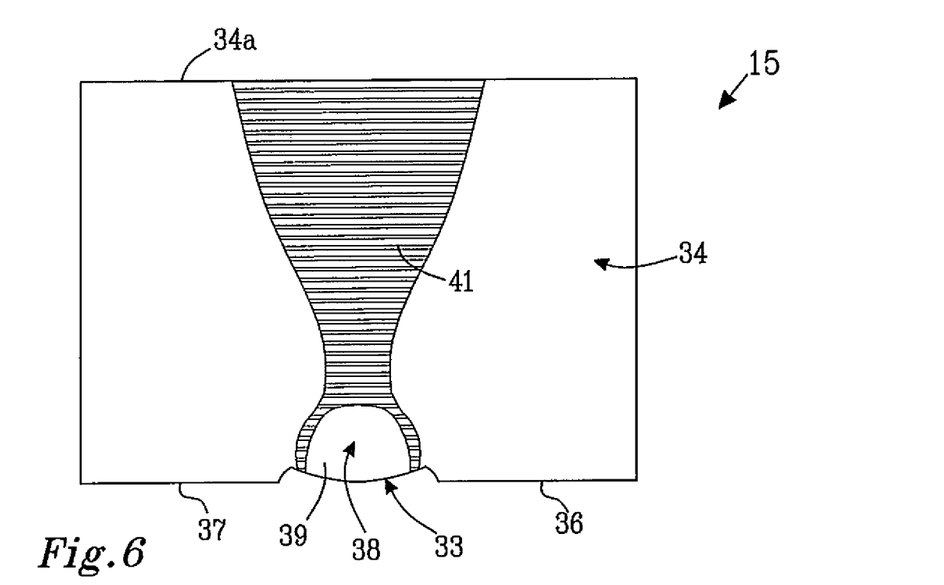
FIG. 6 and is a rear view of the inner pant in FIGS. 4 and 5.

FIGS. 4-6 illustrates a second embodiment of the present invention in which the pant is provided as an inner pant 15 of boxer shorts. Boxer shorts resemble conventional male underwear and are preferred by many users, especially male users. The boxer shorts comprises a garment shell 16 including a front part 17, a back part 18 and a crotch part 19 positioned between the front and back parts. The front and back parts 17 and 18 are joined together to define a three-dimensional pant configuration having a waist opening 20 and a pair of leg openings 21 and 22 with hanging legs 23 and 24. The garment shell 16 may be formed of optional material, such as textile material, to resemble ordinary underwear. The boxer shorts may further comprise an elastic waistband 25 joined to the waist edges of the front and back parts 17 and 18.

The boxer shorts comprise an inner pant 15 according to the present invention adapted to hold an absorbent pad. The inner pant 15 is constructed in a similar manner as the pant 1 described with respect to the embodiment shown in FIGS. 1-3. Thus it comprises a front part 32, a crotch part 33 and a back part 34. It further comprises waist edges 32a, 34a at upper end portions of said front part 32 and said back part 34. The waist edges 32a, 34a of the inner pant is attached to the waist portion of the garment shell of the boxer shorts. The inner pant 15 has a pair of leg openings 36 and 37.

In a corresponding manner as the pant 1 described with respect to the embodiments in FIGS. 1-3 the inner pant 15 comprises a suspending member 38 formed of elastic material and adapted to hold an absorbent pad in close contact with the body of a wearer. It comprises zones of different elasticity, wherein a first elastic zone 39 having a relatively higher elongation is provided in a longitudinally extending central region of the crotch part 33 and the front part 32. A pair of second elastic zones 40a and b having a relatively lower elongation extend along both sides of said first elastic zone 39 at or close to the leg openings 36 and 37 in the crotch part 33 and in the front part 32 along both sides of the first elastic zone 39 of a relatively higher elongation.

The dimensions and characteristics of the first and second elastic zones are the same as described with respect to the embodiment of FIGS. 1-3.

A third elastic zone 41 of a relatively lower elongation as compared to the first elastic zone 39 extends from the crotch part 33 longitudinally along a central region of the back part 34. The third elastic zone 11 has a width w3 that increases towards the waist portion. The third elastic zone 41 and the second elastic zones 40a and b may have the same elongation and be made in the same way. Alternatively they may have differing elongations.

The areas of the front, crotch and back parts 32, 33 and 34 located outside the suspending member 38 may be of the same material as the first elastic zone 39 or of a different optional material. The different areas of the pant having different elastic properties may be joined together, for example by sewing, or they may be formed integrally and seamlessly by knitting technique known in the art and as described above in connection with the pant in FIGS. 1-3.

The inner pant 15 may be attached to the garment shell 16 also in the crotch part in addition to in the waist area. The attachment in the crotch part may be in the form of one or more threads joining together the inner pant to the garment shell 16 in order to prevent the inner pant from sticking to the wearer when the boxer shorts are pulled down.

The minimum crotch width w4 in the pant 1 as well as in the inner pant 15 should be at least 100 mm for a pant adapted to hold an incontinence absorbent pad for adults therein.

Figure 7:
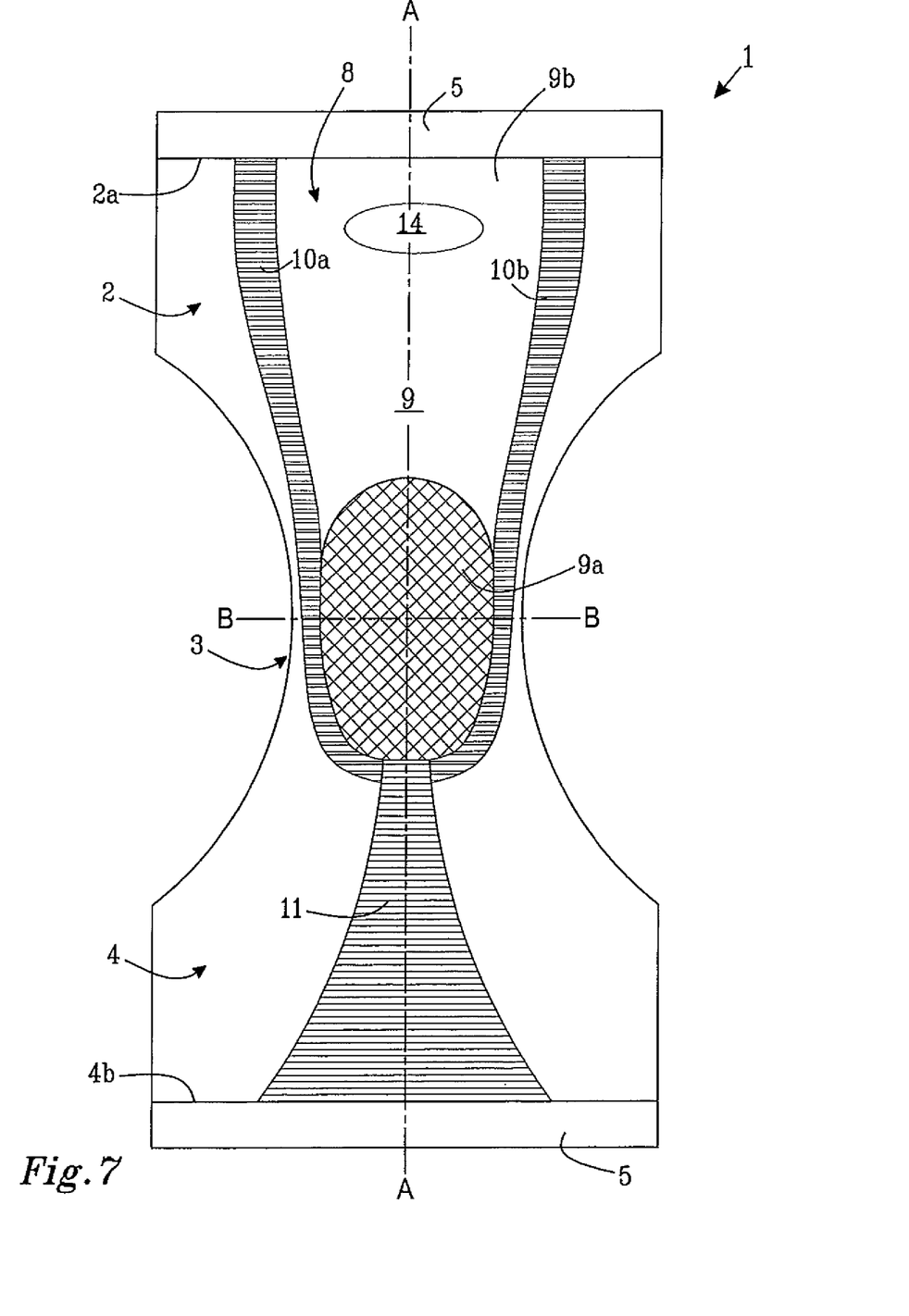
FIG. 7 is a view corresponding to FIG. 3 but showing a modified embodiment of a pant according to the invention.

In the embodiment shown in FIG. 7 the first elastic zone 9 comprises at least two areas of different elasticity, wherein a first area 9a is located in the crotch part 3 of the pant and a second area 9b is located in the front part 2. The first area 9a has a higher elongation and a lower modulus as compared to said second area 9b. It is understood that the first area 9a may extend into the front part 2 and/or that the second area 9b may extend into the crotch part 3.

Test for Determining the Elasticity of Fabrics According to EN 14704-1

A 5×17 cm strip of fabric is placed between two clamps. The distance between the clamps is 10 cm. The strip is stretched and the elongation and force is measured. The clamps stop when the force reaches 5N. The same fabric strip is stretched in two cycles, Evaluation of Results Modulus To calculate modulus a straight line is drawn on the graphs for the load phase and the return phase respectively and the x- and y-coordinates on the straight line drawn are used to calculate the slope. The x-coordinates represent the elongation in mm and the y-coordinates represent the force in N. The slope is the modulus with unit N/mm and is multiplied with 1000, to have N/m as unit:

$$(y2-y1)/(x2-x1) \cdot 1000 = \alpha = modulus$$

The modulus is calculated both for the load phase and the return phase and indicates the elastic properties of the fabric. The higher modulus, the greater pull and fixation there is in the fabric.

Elongation

Elongation is the recorded extension of the strip at the second cycle at 5N applied force.

EXAMPLE

Four pants having areas of different elasticity according to the present invention were tested.

Pant 1: Cotton pant, white colour, having a first zone 9 with first and second areas 9a and 9b as shown in FIG. 7 and having second and third zones 10 and 11. The areas of the pant located outside the first, second and third zones is referred to as "plain zone".

Pant 2: Cotton pant, black colour, and having the same configuration as pant 1.

Pant 3: Polyamide pant, white colour, having a first zone 9 and second zones 10 and 11.

Pant 4: Polyamide pant, black colour, and having the same configuration as pant 3.

The following test results were measured:

TABLE

| Pant | Zone | Modulus load (N/m) | Modulus return (N/m) | Elongation 5N (%) |
|---|---|---|---|---|
| 1 | first zone, (first area) | 16 | 13 | 166 |
| 1 | first zone (second area) | 32 | 16 | 140 |
| 1 | second zone | 93 | 53 | 48 |
| 1 | third zone | 90 | 48 | 49 |
| 1 | plain zone | 80 | 30 | 68 |
| 2 | first zone (first area) | 40 | 20 | 110 |
| 2 | first zone (second area) | 45 | 20 | 96 |
| 2 | second zone | 104 | 50 | 42 |
| 2 | third zone | 100 | 47 | 41 |
| 2 | plain zone | 87 | 47 | 47 |
| 3 | first zone | 25 | 11 | 182 |
| 3 | second and third zones | 49 | 30 | 86 |
| 3 | plain area | 30 | 17 | 145 |
| 4 | first zone | 43 | 25 | 98 |
| 4 | second and third zones | 60 | 40 | 58 |
| 4 | plain zone | 50 | 34 | 78 |

The invention claimed is:

1. A pant comprising:
a front part,
a back part,
a crotch part positioned between said front and back parts,
a waist portion formed at upper end edges of said front part and said back part,
a pair of leg openings,
a suspending member formed of elastic material and arranged in said front part, said crotch part and said back part,
said pant having a longitudinal and a transverse direction,
said suspending member comprises zones of different elasticity, wherein a first elastic zone is provided in a longitudinally extending central region of the crotch part, and a pair of second elastic zones extend along both sides of said first elastic zone at or close to said leg openings in the crotch part,
wherein said second elastic zones have a lower elongation as measured in the longitudinal direction of the pant in comparison with said first elastic zone,
said first and second elastic zones are arranged also in the front part, with said pair of second elastic zones extending along both sides of said first zone also in said front part, a third elastic zone having a lower elongation as measured in the longitudinal direction of the pant in comparison with said first elastic zone, extends longitudinally along a central region of the back part,
wherein said first, second and third elastic zones extend to contact the waist upper end edges of the front and back parts respectively,
wherein a minimum width in the crotch part of the first elastic zone is at least 40 mm and the width of each of the second elastic zones in said crotch part is between 3 and 30 mm, and
wherein said third elastic zone has a width that increases towards the upper waist end edge of the back part.

2. The pant as claimed in claim 1, wherein said pair of second elastic zones diverge from said crotch part to the front part, so that the width of said first elastic zone of relatively higher elongation is gradually reduced from said front part to said crotch part.

3. The pant as claimed in claim 1, wherein the third elastic zone and the second elastic zones have the same elongation.

4. The pant as claimed in claim 1, wherein said pair of second elastic zones converge to continuously form said third elastic zone.

5. The pant as claimed in claim 1, wherein said pair of second elastic zones are separated from said third elastic zone.

6. The pant as claimed in claim 1, wherein the second elastic zones are located at a distance of between 0 and 20 mm from the respective leg opening in at least part of the crotch part.

7. The pant as claimed in claim 1, wherein said first elastic zone comprises at least two areas of different elasticity, wherein a first area is located in the crotch part of the pant and a second area is located in the front part and wherein said first area has a higher elongation as compared to said second area.

8. The pant as claimed in claim 1, wherein the elongation in the first elastic zone is between 50% and 400% higher than in the second elastic zones.

9. The pant as claimed in claim 1, wherein the elongation in the first elastic zone is between 50% and 400% higher than in the third elastic zones.

10. The pant article as claimed in claim 8, wherein the first elastic zone has an elongation at 5N in the range 50% to 300% and the second and/or third elastic zones have an elongation at 5N in the range 25% to 150%.

11. The pant as claimed in claim 1, wherein said first elastic zone has a lower modulus in the load phase and in the return phase as measured in the longitudinal direction of the pant as compared to the second elastic zone.

12. The pant as claimed in claim 1, wherein said first elastic zone has a lower modulus in the load phase and in the return phase as measured in the longitudinal direction of the pant as compared to the third elastic zone.

13. The pant as claimed in claim 11, wherein said first elastic zone has a modulus in the load phase between 10 and 50 N/m and a modulus in the return phase between 8 and 40 N/m and that said second and/or third elastic zones has a modulus in the load phase between 40 and 120 N/m and a modulus in the return phase between 25 and 70 N/m.

14. The pant as claimed in claim 13, wherein the modulus in the load phase and in the return phase in the second elastic zones is between 50% and 600% higher than in the first elastic zone.

15. The pant as claimed in claim 1, wherein the pant is a reusable washable pant adapted to hold a disposable absorbent pad therein.

16. The pant as claimed in claim 1, wherein the pant is an inner pant of a boxer shorts which further comprises an outer garment shell with hanging legs and wherein the inner pant is attached to the outer garment shell at least in a waist portion thereof.

17. The pant as claimed in claim 1, wherein the pant is provided with fastening means for attachment of an absorbent pad.

18. The pant as claimed in claim 1, wherein the zones of different elasticity are formed integrally and seamlessly by knitting.

19. The pant as claimed in claim 1, wherein the width of each of the second elastic zones varies along the crotch part and the front part.

20. The pant as claimed in claim 19, wherein the width of each of the second elastic zones is greater in the front part and is gradually reduced towards the crotch part.

* * * * *